(12) United States Patent
Beckett et al.

(10) Patent No.: US 12,714,479 B2
(45) Date of Patent: Aug. 25, 2026

(54) INTRAMEDULLARY DEVICE FOR ANKLE FUSION

(71) Applicant: Nuvasive Specialized Orthopedics, Inc., San Diego, CA (US)

(72) Inventors: Adam G. Beckett, Mission Viejo, CA (US); Youngsam Bae, Placentia, CA (US); Gabriel Buenviaje, Laguna Hills, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 17/699,116

(22) Filed: Mar. 19, 2022

(65) Prior Publication Data

US 2022/0304730 A1 Sep. 29, 2022

Related U.S. Application Data

(60) Provisional application No. 63/166,850, filed on Mar. 26, 2021.

(51) Int. Cl.
*A61B 17/72* (2006.01)
*A61B 17/00* (2006.01)

(52) U.S. Cl.
CPC ...... *A61B 17/7291* (2013.01); *A61B 17/7225* (2013.01); *A61B 17/7241* (2013.01);
(Continued)

(58) Field of Classification Search
CPC ............ A61B 17/7291; A61B 17/7225; A61B 17/7216; A61B 2017/564; A61B 17/7233;
(Continued)

(56) References Cited

U.S. PATENT DOCUMENTS 7,753,915 B1 * 7/2010 Eksler ................ A61B 17/7016 606/86 R
8,118,952 B2 * 2/2012 Gall .................. A61B 17/8004 148/563

(Continued)

FOREIGN PATENT DOCUMENTS

WO WO-2016175893 A1 * 11/2016 ....... A61B 17/12013
WO WO-2017132646 A1 * 8/2017 ............ A61B 17/62

(Continued)

OTHER PUBLICATIONS

Vogt B, et al. Tibial lengthening using a retrograde magnetically driven intramedullary lengthening device in 10 patients with pre-existing ankle and hindfoot fusion. Acta Orthop. Dec. 2020;91(6):761-769. doi: 10.1080/17453674.2020.1807222. Epub Aug. 24, 2020. PMID: 32835564; PMCID: PMC8023964. (Year: 2020).*

*Primary Examiner* — Eduardo C Robert
*Assistant Examiner* — Anna V. Little

(57) ABSTRACT

An aspect of the disclosure relates to an intramedullary device configured for ankle fusion. The intramedullary device for ankle fusion includes: a housing configured to be coupled to a calcaneus bone; and a rod configured to be coupled to a tibia bone, wherein a distal end of the housing includes an external thread. The rod is configured for telescopic movement relative to the housing, and to retract relative to the housing to cause ankle fusion. After fusion is achieved, the rod can be distracted to correct a limb length discrepancy.

15 Claims, 13 Drawing Sheets

(52) U.S. Cl.
CPC ............... *A61B 2017/00876* (2013.01); *A61B 2017/00991* (2013.01)

(58) Field of Classification Search
CPC .............. A61B 17/7241; A61B 17/725; A61B 17/7283
See application file for complete search history.

(56) References Cited

U.S. PATENT DOCUMENTS

| | | | | |
|---|---|---|---|---|
| 8,382,756 | B2 | 2/2013 | Pool et al. | |
| 8,734,488 | B2 | 5/2014 | Pool et al. | |
| 9,044,281 | B2 | 6/2015 | Pool et al. | |
| 9,078,711 | B2 | 7/2015 | Quick | |
| 9,248,043 | B2 | 2/2016 | Payne et al. | |
| 10,835,290 | B2 | 11/2020 | Cheng et al. | |
| 10,918,425 | B2 | 2/2021 | Schwardt et al. | |
| 11,246,694 | B2 | 2/2022 | Cheng | |
| 2002/0072748 | A1* | 6/2002 | Robioneck | A61B 17/7216 606/64 |
| 2005/0101958 | A1* | 5/2005 | Adam | A61B 17/72 606/62 |
| 2006/0200141 | A1* | 9/2006 | Janna | A61B 17/7291 606/62 |
| 2007/0233101 | A1* | 10/2007 | Metzinger | A61B 17/72 606/62 |
| 2008/0221577 | A1* | 9/2008 | Elghazaly | A61B 17/7241 606/62 |
| 2009/0112263 | A1* | 4/2009 | Pool | A61B 17/707 600/587 |
| 2010/0094306 | A1* | 4/2010 | Chang | A61B 17/7023 606/90 |
| 2010/0114315 | A1* | 5/2010 | Manderson | A61B 17/863 606/301 |
| 2011/0054473 | A1* | 3/2011 | Brigido | A61B 17/1725 606/86 R |
| 2011/0166609 | A1* | 7/2011 | Duggal | A61B 17/683 606/328 |
| 2011/0196435 | A1* | 8/2011 | Forsell | A61B 17/7062 606/86 R |
| 2011/0282397 | A1* | 11/2011 | Richter | A61B 17/1725 606/301 |
| 2012/0215222 | A1* | 8/2012 | Yapp | A61B 17/1725 606/57 |
| 2012/0330313 | A1* | 12/2012 | Grady | A61B 17/7225 606/64 |
| 2013/0245626 | A1* | 9/2013 | Lavi | A61B 17/72 606/62 |
| 2013/0310835 | A1* | 11/2013 | Gall | A61B 17/7233 606/62 |
| 2013/0338714 | A1 | 12/2013 | Chang et al. | |
| 2014/0228845 | A1* | 8/2014 | Gorsline | A61B 17/7291 606/62 |
| 2014/0313745 | A1* | 10/2014 | Chen | F21V 14/06 362/311.03 |
| 2015/0313745 | A1* | 11/2015 | Cheng | A61B 17/7216 602/19 |
| 2016/0113683 | A1 | 4/2016 | Cheng | |
| 2016/0183994 | A1* | 6/2016 | Quach | A61B 17/7017 606/90 |
| 2017/0224394 | A1* | 8/2017 | Tandiya | A61B 17/7241 |
| 2017/0296241 | A1* | 10/2017 | Garlock | A61B 17/7291 |
| 2019/0046252 | A1* | 2/2019 | Skinlo | A61B 17/1675 |
| 2019/0358046 | A1* | 11/2019 | Ehmke | A61B 17/7216 |
| 2021/0038269 | A1* | 2/2021 | Kearns | A61B 17/1775 |

FOREIGN PATENT DOCUMENTS

| | | | | |
|---|---|---|---|---|
| WO | WO-2017223304 | A1 * | 12/2017 | |
| WO | 2020163800 | A1 | 8/2020 | |
| WO | WO-2020176874 | A9 * | 10/2020 | A61B 17/68 |

* cited by examiner

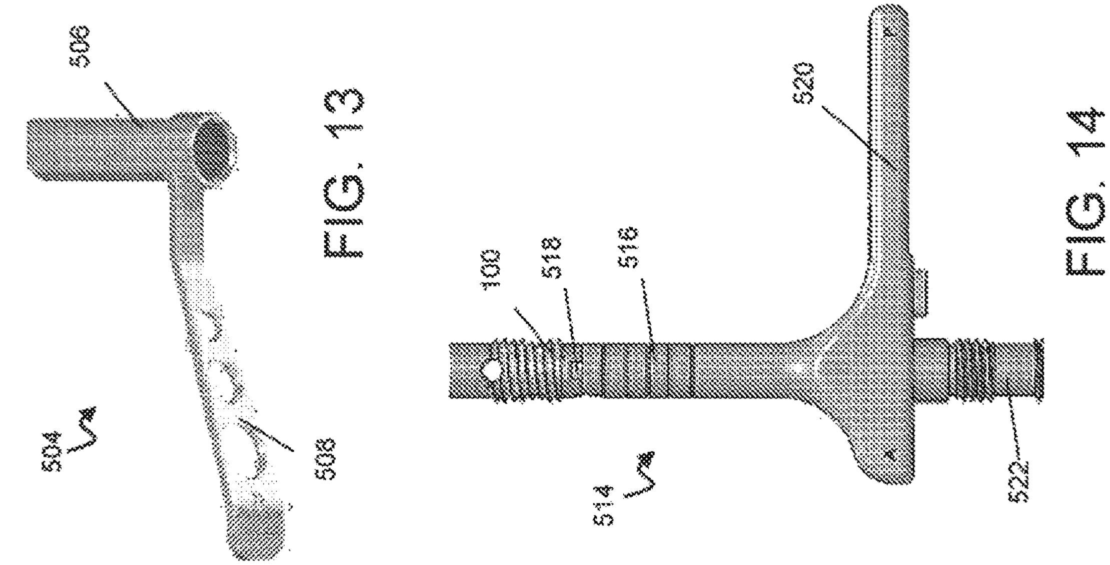
FIG. 13
FIG. 14
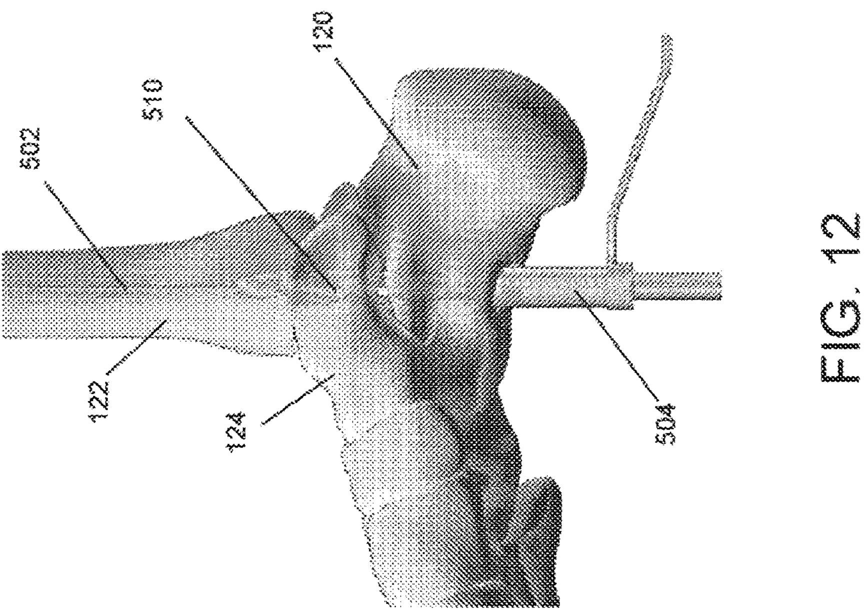
FIG. 12

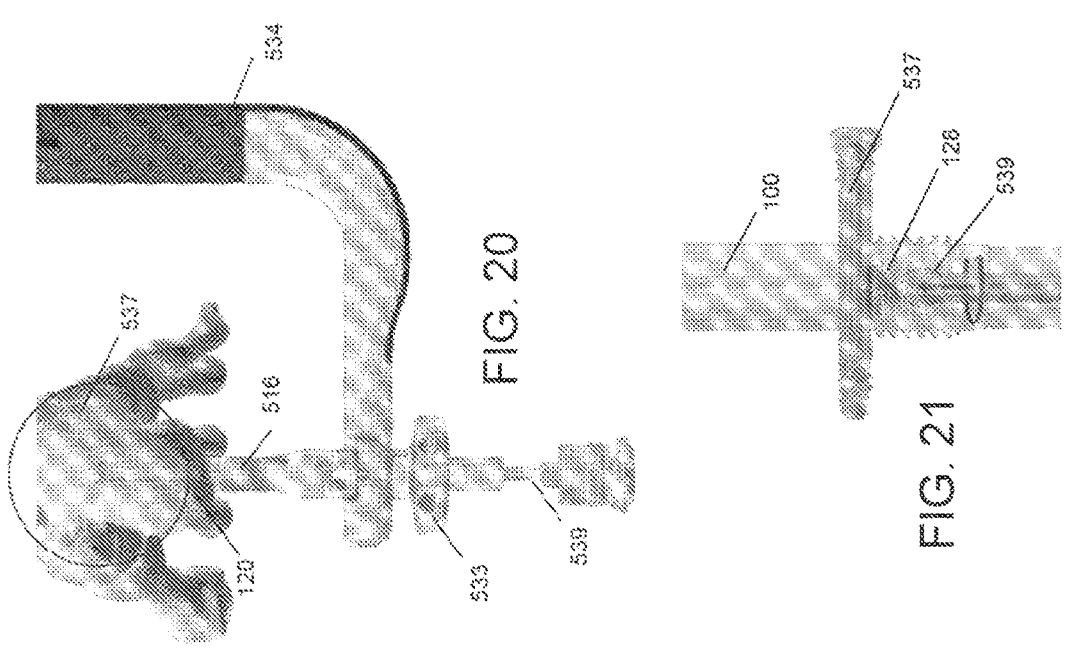
FIG. 20
FIG. 21
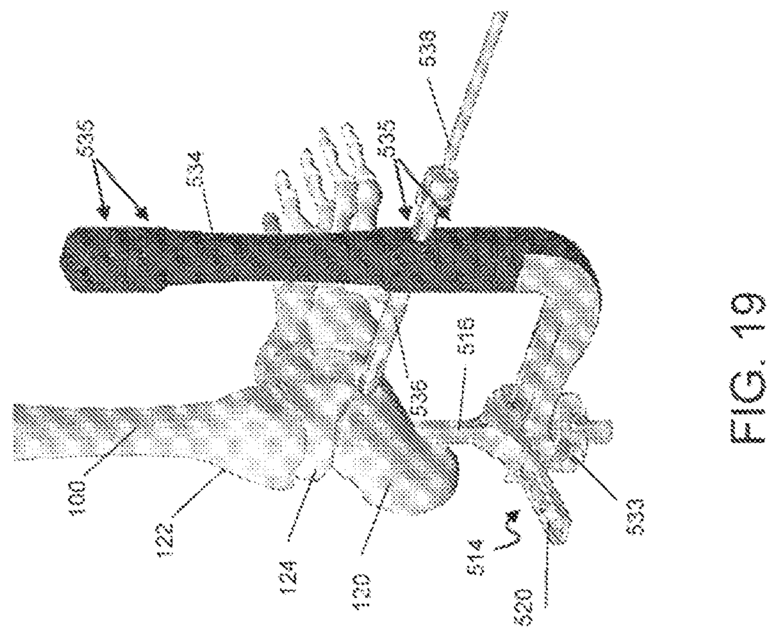
FIG. 19

INTRAMEDULLARY DEVICE FOR ANKLE FUSION

CROSS REFERENCE TO RELATED APPLICATIONS

The present patent application claims the benefit under 35 U.S.C. § 119(e) of U.S. Provisional Patent Application Ser. No. 63/166,850, filed on Mar. 26, 2021. The foregoing application is incorporated by reference as though fully set forth herein.

TECHNICAL FIELD

The subject matter described herein relates to an intramedullary device, system, and associated methods.

BACKGROUND

Treating failed ankle joints is challenging due to poor stability and/or bone loss. Ankle fusion or ankle arthrodesis is a type of orthopedic surgery that fuses together the ankle bones in one piece. Current ankle fusion methods often result in mal-unions or fail to heal, resulting in the need for limb salvage. Current limb salvage procedures include external fixators in which an external fixation frame is attached to the bone segments by pins which pass through the skin. The pins can be sites for infection and are often painful for the patient, as the pin placement site remains a somewhat open wound or "pin tract" throughout the treatment process. The external fixation frames are also bulky, making it difficult for patient to comfortably sit, sleep and move. If the limb is salvaged, patients are often left with limb length discrepancies. The alternative to limb salvage is limb amputation.

SUMMARY

A first aspect of the disclosure relates to an intramedullary device for ankle fusion. The intramedullary device includes: a housing configured to be coupled to a calcaneus bone; and a rod configured to be coupled to a tibia bone, the rod configured for telescopic movement relative to the housing, wherein a distal end of the housing includes an external thread to aid boney fixation.

A second aspect of the disclosure relates to a method. The method includes providing an intramedullary device including a housing and a rod configured to be moved relative to the housing; coupling the rod to a tibia bone of a patient; coupling the housing to a calcaneus bone of a patient; and causing the rod to retract relative to the housing to cause compression about the ankle joints of the patient to cause ankle fusion.

A third aspect of the disclosure relates to a system for ankle fusion. The system includes: an intramedullary device including: a housing configured to be coupled to a calcaneus bone; and a rod configured to be coupled to a tibia bone, the rod configured for telescopic movement relative to the housing, wherein a distal end of the housing includes an external thread; and an external adjustment device configured to cause retraction and distraction of the rod relative to the housing.

BRIEF DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 12 shows a guidewire, reamer and soft tissue protector according to embodiments of the disclosure;

FIG. 13 shows a perspective view of the soft tissue protector according to embodiments of the disclosure;

FIG. 14 shows a side view of the insertion handle mated with the intramedullary device according to embodiments of the disclosure;

FIGS. 18-19 show using the guide for insertion of the lateral-medial calcaneus fixation screws according to embodiments of the disclosure;

FIG. 20 shows using a driver to set the set screw according to embodiments of the disclosure;

FIG. 21 shows an enlarged view of the driving of the set screw according to embodiments of the disclosure;

DETAILED DESCRIPTION

The present disclosure describes various embodiments of an intramedullary device, system and associated methods. The devices, systems and methods described herein can be used for controlled compression across tibio-talo-calcaneal (TTC) joints in order to achieve fusion. The nail is pre-distracted and provides non-invasive compression via retraction of the device controlled by an external adjustment device. After fusion, if there is any limb length discrepancy, the device can then be used to lengthen the limb by creating an osteotomy in the tibia and performing distraction osteogenesis.

Figures 1, 2:
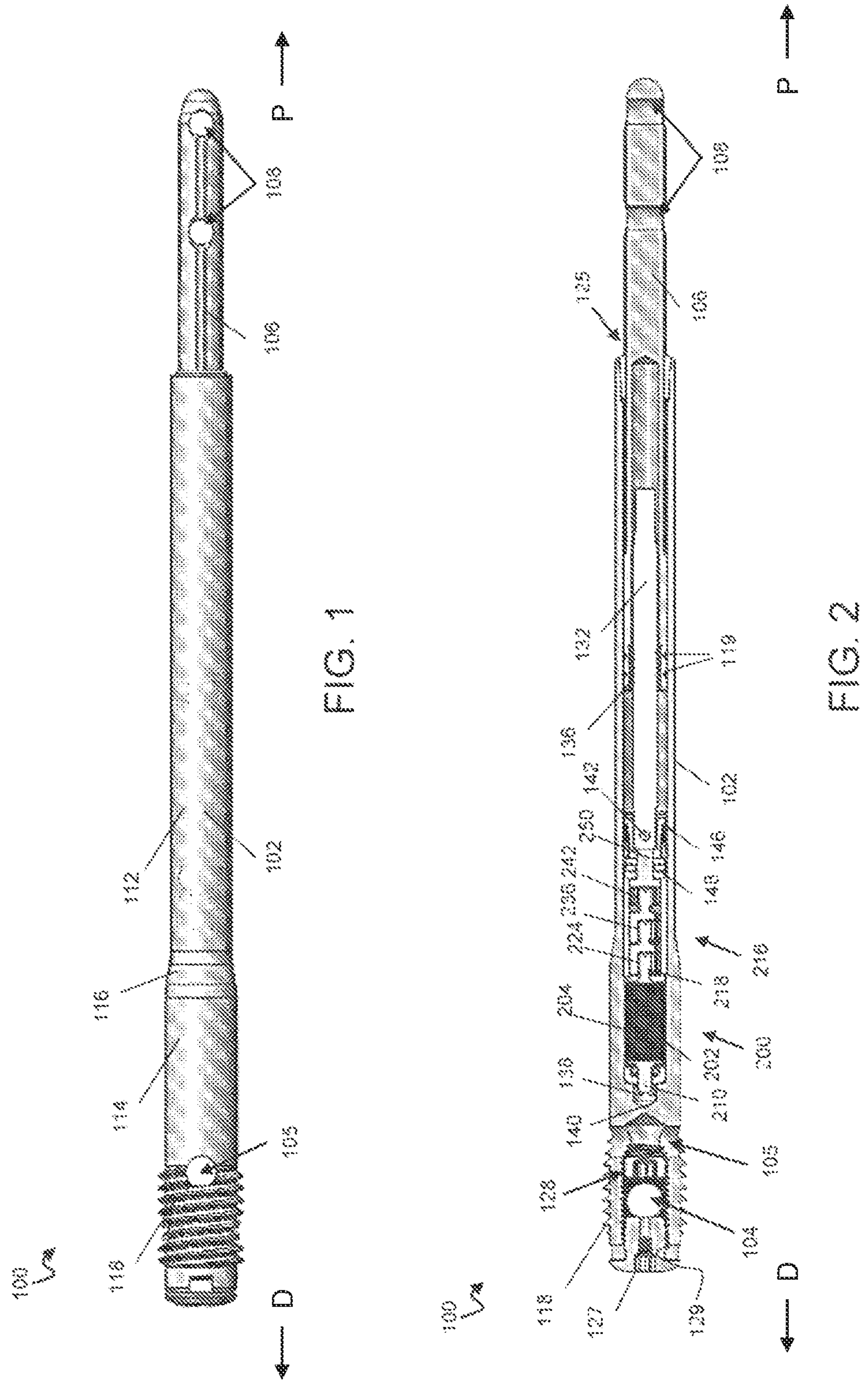
FIG. 1 shows a side view of an intramedullary device according to embodiments of the disclosure.
FIG. 2 shows a cross-sectional view of the intramedullary device of FIG. 1.

FIG. 1 shows a top-down view of an intramedullary distraction device 100 and FIG. 2 shows a cross-sectional view of the device 100 according to embodiments of the disclosure. As shown, the device 100 includes a housing 102 having at least one fixation aperture (two shown, 104, 105) at a distal end D thereof, and a rod 106 having at least one fixation aperture 108 (two shown) at a proximal end P thereof. For example, the housing 102 can have a first fixation aperture 104 and a second fixature aperture 105 extending normal to the first fixation aperture 104 such that one fixation aperture 105 is configured to extend lateral to medial and the other fixation aperture 104 is configured to extend posterior-anteriorly. The rod 106 can have a first fixation aperture 108 extending parallel to a second fixation aperture 108. However, any configuration of fixation apertures is contemplated without departing from aspects of the disclosure. The rod 106 is configured to distract and retract relative to the housing 102. In some embodiments, at least one fixation aperture 104, 105, 108 can be a locking screw hole having internal threads (not shown) for threadingly engaging with a thread on a head of a fixation screw. In some embodiments, all fixation apertures 104, 105, 108 may have internal threads. In some embodiments, none of the fixation apertures 104, 105, 108 have internal threads and none of the heads of the fixation screws have threads.

As shown in FIG. 1, the housing 102 includes a first portion 112 having a first diameter and a second portion 114 having a second diameter greater than the first diameter 112. One or more ramps 116 can interface between portions 112, 114. Portion 112 can have a diameter of approximately 10 millimeters (mm) to approximately 13 mm and portion 114 can have a diameter of approximately 12 mm to approximately 15 mm. However, any range of diameters for portions 112, 114 can be used without departing from aspects of the disclosure. The rod 106 can have a diameter smaller than portion 112 such that rod 106 can be telescopically received within the housing 102. For example, the rod 106 can have a diameter of approximately 7 mm to approximately 10 mm. However, any range of diameters for the rod 106 can be used without departing from aspects of the disclosure so long as the rod 106 is capable of being received within the housing 102.

As also shown in FIGS. 1-2, the housing 102 also includes an external thread 118. The external thread 118 at a distal end D of the housing 102 of device 100 increases calcaneal fixation stiffness. In some embodiments, the external thread 118 is a double lead thread. However, other types of thread forms may also be used without departing from aspects of the disclosure. For example, in some embodiments, a single or triple lead thread can be used. In some embodiments, the external thread 118 can have a thread pitch of approximately 2 mm. However, any other range of thread pitches can also be used without departing from aspects of the disclosure.

Figure 4:
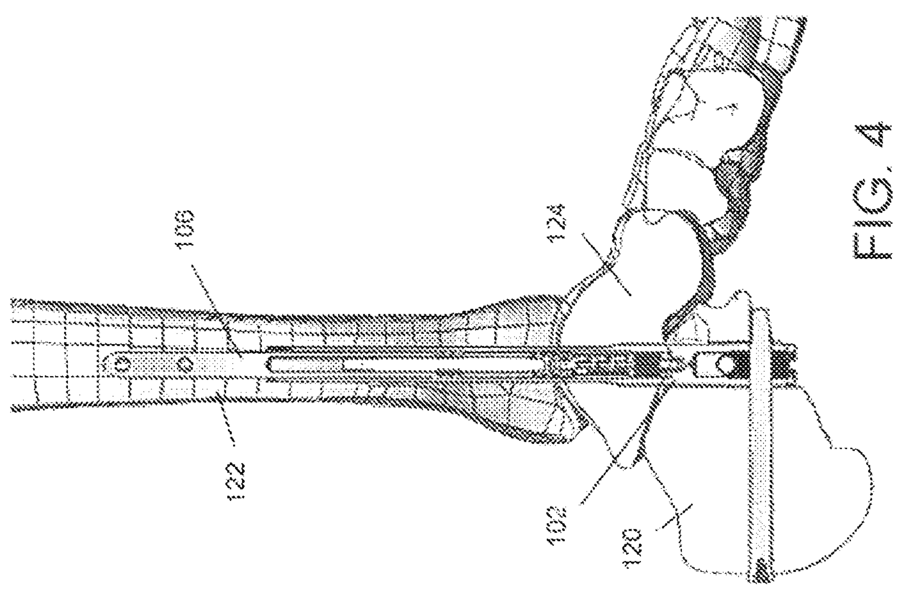
FIG. 4 shows a cross-sectional view of the intramedullary device of FIG. 1 implanted into a patient.

The housing 102 is configured to be fixed to a bone at a first location and the rod 106 is configured to be fixed to the bone at a second location. More specifically, as shown in FIG. 4, the housing 102 is fixed to the calcaneus 120 and the rod 106 is fixed to the tibia 122. The device 100 extends across the talus 124. In order to cause ankle fusion, the device 100 is pre-distracted prior to insertion/implantation. Once fixed in place, the device 100 provides controlled compression until the desired fusion is achieved. The device 100 is configured to allow controlled, precise translation of the rod 106 relative to the housing 102 by non-invasive remote control, and thus controlled, precise translation of the bone segment that is secured to the rod 106.

Over the treatment period, the bone may be regularly compressed. Regularly compressed is meant to indicate that compression occurs on a regular or periodic basis which may be on the order of every day, every few days, or every few weeks. In some embodiments, the compression occurs every 2-4 weeks. The device 100, as disclosed in more detail below, has a magnetic drive system, which allows the rod 106 to be telescopically retracted relative to the housing 102, thus forcing the first section and the second section of the bone closer together to encourage fusion.

Turning to FIG. 2, the housing 102 has an opening 125 at a proximal end thereof for receiving the rod 106. One or more o-rings 119 can be positioned about the rod 106 between the rod 106 and the housing 102. The o-rings 119 may be made of silicone, ethylene propylene diene monomer (EPDM) rubber, or other rubber materials, and may be coated with silicone oil, to aid in lubricity. In some embodiments, a portion of the outer surface of the rod 106 and/or a portion of an internal surface of the housing 102 may be recessed to accommodate the o-ring(s) 119. The o-ring(s) 119 can help facilitate proper sealing between the housing 102 and the rod 106 so that bodily fluid does not enter the housing 102 when the device 100 is implanted.

The housing 102 is sealably closed at the distal end thereof by the attachment of an end cap 127. The end cap 127 may be attached to the housing 102 by means of welding, adhesive bonding or other joining techniques. The end cap 127 can also threadingly engage with threads 129 positioned about an inner surface of the housing 102 at the distal end of the device 100. Further, an o-ring (not shown) may be provided between the end cap 127 and the housing 102 to help provide a seal. A set screw 128 may also be positioned within the housing 102 adjacent the end cap 127, or more specifically, on an opposing side of the aperture 104 relative to the end cap 127 so that the end cap 127 and the set screw 128 are separated by the aperture 104 and/or a fixation screw (not shown) positioned within the aperture 104. The end cap 127 acts as a set screw for the fixation screw positioned within the aperture 104 that extends in a posterior-anterior direction, and the set screw 128 acts as a set screw for the second fixation screw positioned within the adjacent aperture 105 that extends in a medial-lateral direction. Together, the end cap 127 and set screw 128 maintain the positions of the fixation screws disposed within the fixation apertures 104, 105. Additionally, the end cap 127 provides a flush end to the device 100 to interface with the patient.

Figure 5:
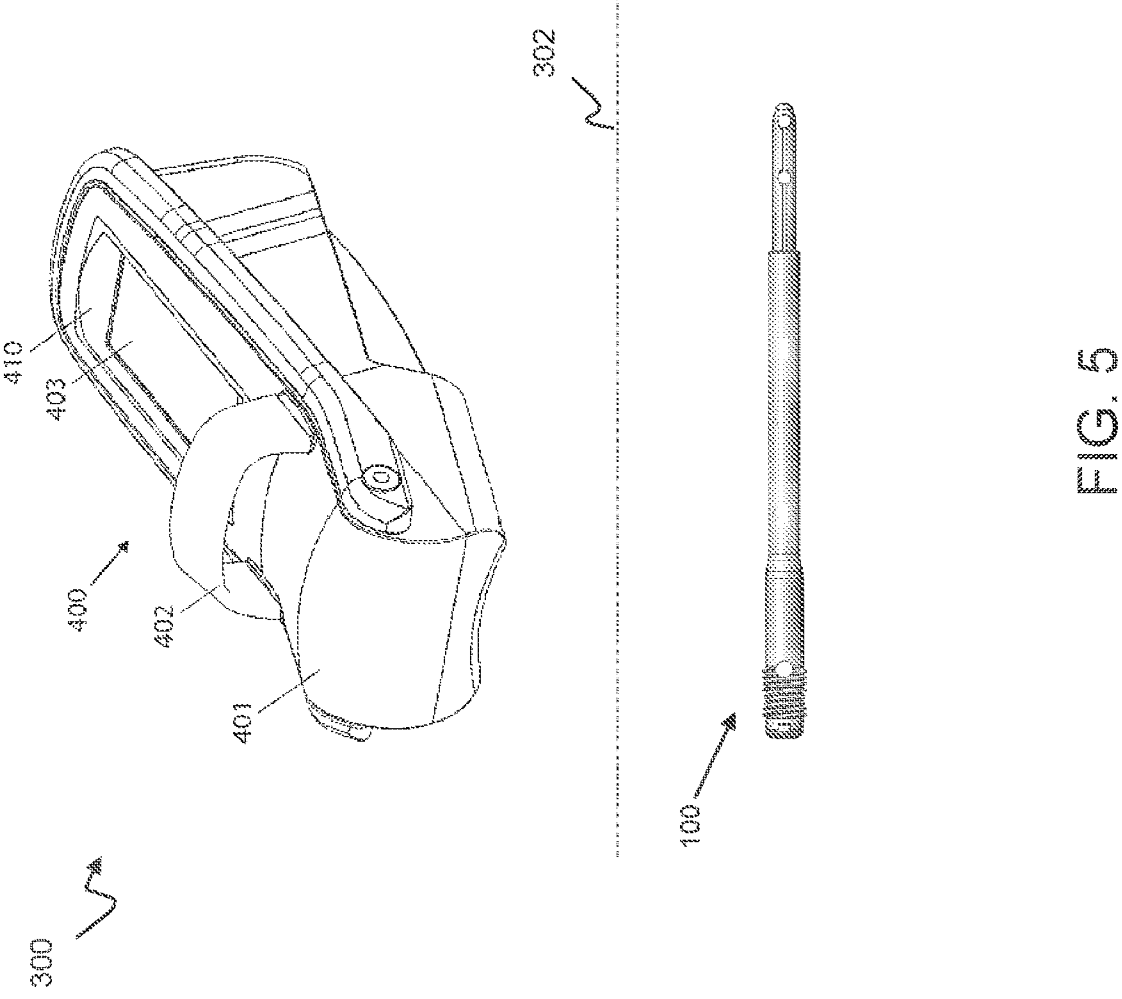
FIG. 5 shows a perspective view of a system for non-invasively adjusting a first bone portion and a second bone portion according to aspects of the disclosure.

In use, the rod 106 is driven from the housing 102 by means of a lead screw 132 which turns inside a nut 136 that is secured to an inner surface adjacent to a cavity of the rod 106 in which the lead screw 132 is disposed. The nut 136 is positioned between the lead screw 132 and the rod 106. The lead screw 132 is mechanically coupled, in an indirect manner, to a cylindrical permanent magnet 202 contained within the housing 102. As explained in more detail herein, rotation of the cylindrical permanent magnet 202, which is magnetically driven by an external adjustment device 400 as illustrated in FIG. 5, effectuates rotation of the lead screw 132. Rotation of the lead screw 132 then translates into axial movement of the rod 106 relative to the housing 102.

Figure 3:
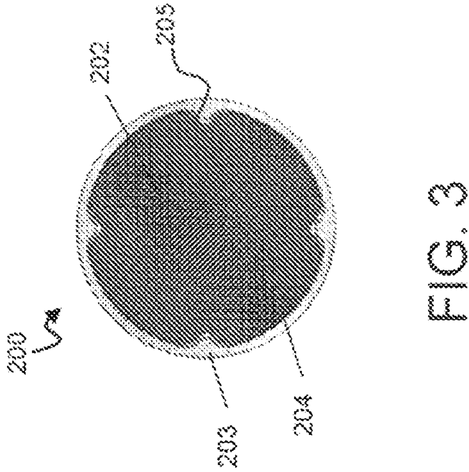
FIG. 3 shows a cross-sectional view of a magnetic assembly according to embodiments of the disclosure.

The cylindrical permanent magnet 202 is fixedly contained within a magnet casing 204 using, for example, an adhesive such as an epoxy. However, in other embodiments, the cylindrical permanent magnet 202 is held within the magnet casing 204 via tabs formed within one of the cylindrical permanent magnet 202 or the magnet casing 204 that matingly engage with complementary grooves formed within the other one of the cylindrical permanent magnet 202 and the magnet casing 204. For example, as shown in FIG. 3, tabs 203 are formed within the magnet casing 204 and matingly engage with grooves 205 formed within the cylindrical permanent magnet. The magnet casing 204 rotates relative to the housing 102. The cylindrical magnet 202 may be a rare earth magnet such as Nd—Fe—B and may be coated with Parylene or other protective coatings in addition to being protected within the magnet casing 204, for example hermetically potted with epoxy. Referring back to FIG. 2, the magnet casing 204 contains an axle 210 on the distal end thereof which attaches to the interior of a radial bearing 138. This arrangement allows the cylindrical magnet 202 to rotate with minimal torsional resistance. A maintenance member 140 may be positioned in proximity to and/or adjacent to the cylindrical permanent magnet 202. The maintenance member 140 keeps the device 100 from being accidentally adjusted by movements of the patient. The maintenance member 140 is positioned proximate and axially spaced from the magnet 202. The maintenance member 140 is made from a magnetic material, such as 400 series stainless steel. The maintenance member 140 can, for example, be generally cylindrical in shape having two spaced apart tabs separated by gaps. When the device 100 is not being adjusted (e.g., using an external adjustment device), the magnetic poles of the radially-poled cylindrical magnet 202 are magnetically attracted to the tabs. However, when the magnet 202 is forced to rotate due to the effect of a sufficiently large rotating magnetic field, the magnet 202 overcomes the smaller attractions of the tabs. Additional details of the maintenance member can be found in U.S. application Ser. No. 16/046,909, filed Jul. 26, 2018, and issued as U.S. Pat. No. 10,918,425, which is incorporated herein by reference as if set forth in its entirety. Other maintenance members such as those disclosed in U.S. Pat. No. 8,734,488, filed Aug. 4, 2011, and U.S. application Ser. No. 13/525,058, filed Jun. 15, 2012 and published as U.S. Pat. App. Pub. US 2013/0338714 A1 can also be used, each of which are incorporated herein by reference as if set forth in its entirety.

At its proximal end, the magnet housing 204 includes an axle 218 which couples the magnet housing 204 to a gear assembly 216. More specifically, the axle 218 is attached to a first planetary gear set 224. The axle 218 includes the sun gear of the first planetary gear set 224, the sun gear turning the planetary gears of the first planetary gear set 224. The first planetary gear set 224 serves to reduce the rotational speed and increase the resultant torque delivery from the cylindrical magnet 202 to the lead screw 132. A second planetary gear set 236 and a third planetary gear set 242 are also shown between the first planetary gear set 224 and the lead screw 132, for further speed reduction and torque augmentation. The torque applied on the magnetic assembly 200 by the action of the rotating magnetic field on the cylindrical permanent magnet 202, is therefore augmented on the order of 64 times in terms of the turning torque of the lead screw 132. This allows the rod 106 to be able to move with high precision. Because of the 64:1 gear ratio, the device 100 is able to axially displace the bone segment coupled to the rod 106 against severe resisting forces, for example those created by soft tissue. The number of planetary gear sets and/or the number of teeth in the gears may be adjusted, in order to achieve the desired speed and torque delivery.

The planetary gear sets 224, 236, 242 output to a planetary gear output shaft 250. The planetary gear output shaft 250 extends through a thrust bearing 148 and is secured (e.g., by welding or the like) to a lead screw coupling cap 146. The lead screw 132 is secured to the lead screw coupling cap 146 by a locking pin 142, which extends through a hole in the lead screw 132 and holes in the lead screw coupling cap 146. A locking pin retainer (not shown) can optionally be included to hold this assembly together and may include a cylinder that surrounds the locking pin 142. Attaching the lead screw 132 to the rest of the magnet/gear assembly in this manner, assures that the design is not over-constrained, and thus that the lead screw 132 does not gall with the nut 136. In addition, a biocompatible grease, for example KRYTOX, may be used on the moving parts (e.g., lead screw 132, nut 136, bearings 148, housing 102, and distraction rod 106) in order to minimize frictional losses. The lead screw 132 is able to freely rotate within a cavity of the distraction rod 106, and only need engage with the short length of the nut 136, this feature also minimizing frictional losses.

The thrust bearing(s) 148 serves to protect the magnet assembly 200 and the gear assembly 216 of the drive from any significant compressive or tensile stresses. When there is a compressive force on the device, for example, when distracting a bone, and thus resisting the tensile strength of the soft tissues, the thrust bearing(s) 148 abuts against retainer clip(s) and/or ledge(s) within the housing 102. Additionally, in compressive applications, there would be tensile force on the device 100 and the thrust bearing(s) 148 would abut against the retainer clip(s) or a ledge. In both situations, the thrust bearings 148 and ledge(s) take the large stresses, not the magnet assembly 200 or gear assembly 216 of the drive system.

Actuation of the actuator magnet assembly 200 can be caused and controlled by an external adjustment device such as those described in U.S. Pat. No. 8,382,756, filed on Nov. 10, 2009; U.S. Pat. No. 9,248,043, filed Jun. 29, 2011; U.S. Pat. No. 9,078,711, filed on Jun. 6, 2012; U.S. Pat. No. 9,044,281, filed on Oct. 18, 2012; U.S. Pat. No. 9,248,043, filed on Jun. 29, 2011; U.S. Pat. No. 11,246,694, filed on Apr. 28, 2015; U.S. application Ser. No. 14/932,904, filed on Nov. 4, 2015; U.S. Pat. No. 10,835,290, filed on Jun. 8, 2018; and International Pat. App. No. PCT/US2020/017338, filed on Feb. 7, 2020, all of which are incorporated herein by reference as if set forth in their entirety. Thus, the disclosure also relates to a system 300 (FIG. 5) for adjusting the position of two bone portions relative to each other. The system 300 can include the device 100 fixed within a patient 302 and an external adjustment device 400 positioned external to the patient 302. The external adjustment device 400, may include a housing 401 having a handle 402 and a display 403. The handle 402 is shown extending upwardly from the housing 401. In some embodiments, the display 403 may be integrated with the housing 401 of the external adjustment device 400. In the illustrated embodiment, the external adjustment device 400 is configured to receive a removable controller 410 having a display 403, with the display 403 being an integral part of the removable controller 410.

According to an exemplary embodiment, the controller 410 may be a handheld electronic device. The handheld electronic device may be, for example, a smartphone, a tablet, or any other known handheld electronic device. The handheld electronic device may contain and may be operatively connected to a display and/or one or more wireless communication protocols (e.g., Wi-Fi or Bluetooth® (Bluetooth® is a registered trademark of Bluetooth SIG, Inc., Kirkland, WA)). The display of the handheld electronic device may be disposed adjacent to a top surface of the external adjustment device 400, such that the display 403 can communicate information to and receive instructions from a user during use.

For example, in some embodiments the display 403 may present to a user a graphical user interface (GUI). The display 403 may include one or more of a touchscreen or touchscreen technology, including, for example, capacitive touchscreen technology. The GUI may communicate adjustment instructions to a user which may correspond to a treatment regimen to guide the user in adjusting the adjustable implant in accordance with the treatment regimen. Additionally, the GUI may include one or more touchscreen digital buttons configured to activate and control the external adjustment device 400.

Figure 6:
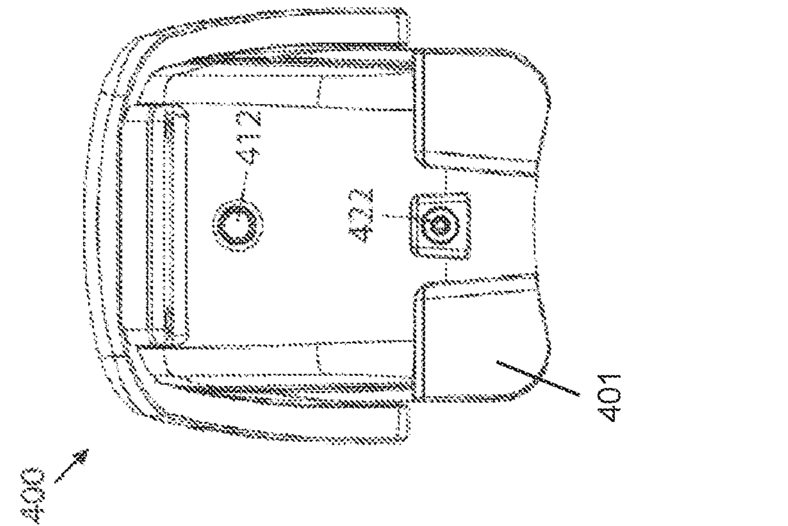
FIG. 6 shows a front view of an external adjustment device according to embodiments of the disclosure.

FIG. 6 shows a front view of the external adjustment device 400, the external adjustment device 400 including a power supply input 422 and a data connection port 412. Additionally, a bottom surface of the housing 401 is shown including a curvature configured to form to a patient's body and minimize a distance (GAP) between the magnet 440 (FIG. 7) and a magnet 202 (FIG. 2) of the device 100. The power supply input 422 may be configured to removably receive an AC power supply. The data connection port 412 may be configured to removably receive a data communication cable. The data communication cable may be configured to connect the external adjustment device 400 to a tertiary device to perform one or more of functions such as, e.g., updating the controller 410 software and downloading data from the controller 410.

Figure 7:
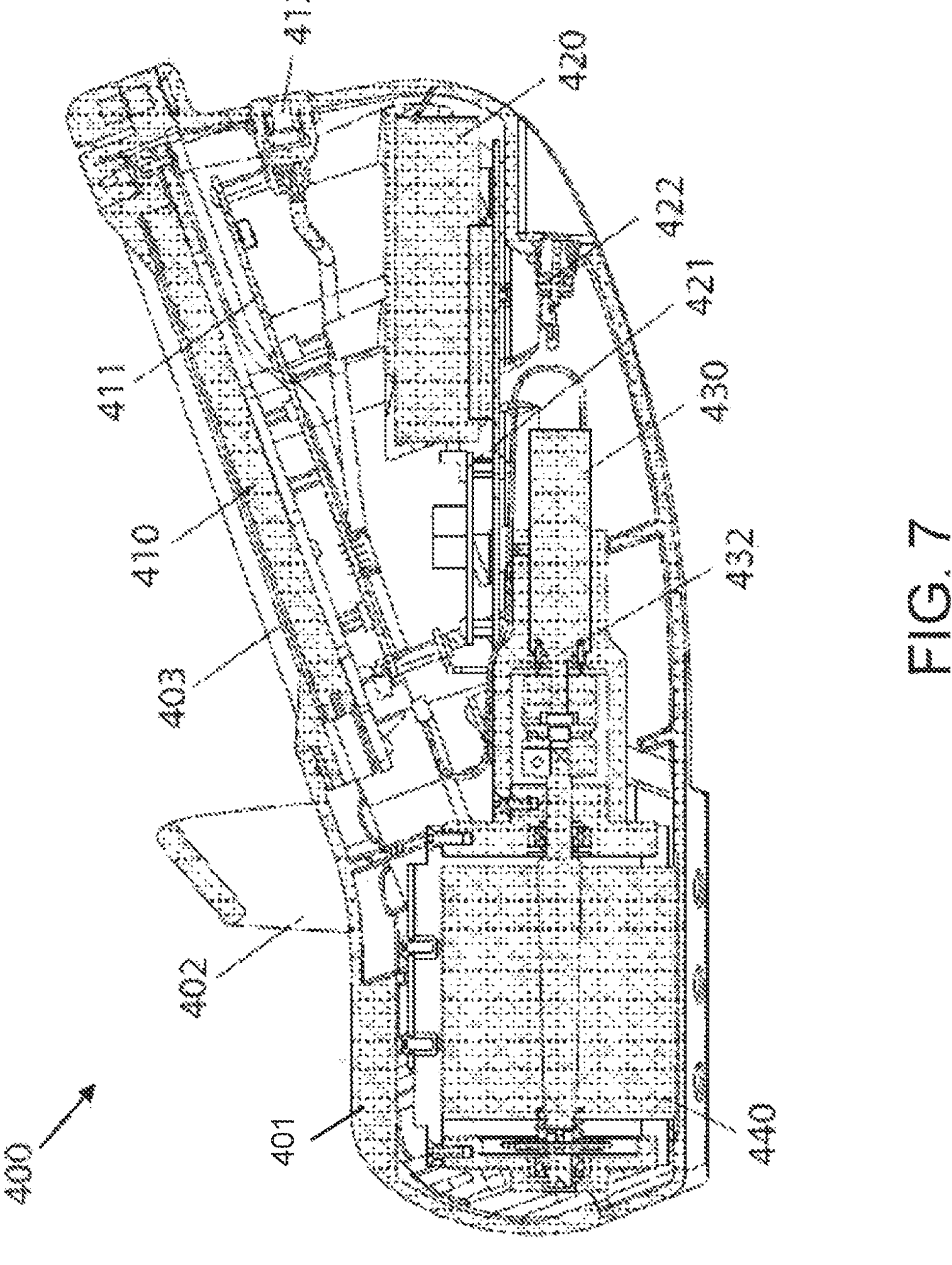
FIG. 7 shows a cross-sectional side view of the external adjustment device according to embodiments of the disclosure.

FIG. 7 shows a cross-sectional side view of the external adjustment device 400 in accordance with the first embodiment. The external adjustment device 400 shown including the housing 401, the controller 410, an internal power storage device 420, a actuator 430, and at least one magnet 440.

The internal power storage device 420 and wireless communication capabilities of the controller 440, may provide for wireless operation of the external adjustment device 400. The internal power storage device 420 may negate the need for a power cord during operation. The controller 410 may provide a low voltage control system negating the need for a bulky external control module. Wireless communication capabilities, for example one or more of radio frequency (RF), Wi-Fi, or Bluetooth®, may enable the external adjustment device 400 and the controller 410 for remote operation. The remote operation may be achieved, e.g., by one or more of a tertiary device in the same room, and across the internet by a tertiary device on the other side of the globe.

In some embodiments, the controller 410 may be a control board disposed within the housing 401 of the external adjustment device 400. The display 403 may include any type of display 403, including for example: LED, LCD, OLED, and any other known display and touchscreen technology. The control interface board 411 may contain or be in communication with one or more communication circuit, for example, one or more of Wi-Fi, cellular networks, or Bluetooth®, enabling communication between the external adjustment device 400 and one or more tertiary devices.

In FIG. 7, the controller 410 is shown operably connected to a controller interface board 411 by at least one interconnect. In some embodiments, this connection may be established via a physical connection as illustrated, and in some embodiments, via a wireless connection, for example, Bluetooth®. The control interface board 411 may be further connected to one or more of a power interface board 421, the power storage device 420, and the actuator 430.

The controller 410 may be remotely accessible and remotely controllable by a tertiary device allowing for remote operation of the external adjustment device 400 by a user from outside of a sterile field.

The external adjustment device 400 is also shown including an internal power storage device 420. The power storage device 420 may include a battery, a capacitor, and any other power storage device known and used in the art. The power storage device may be rechargeable and the external adjustment device 400 may include a recharging circuit configured to recharge the power storage device 420 using an external power source. The external power source, for example a power supply, may be operably connected to the recharging circuit of the power storage device via the power supply input. The power storage device 420, and/or at least a portion of the recharging circuit, may be disposed adjacent to a surface of the external adjustment device 400, enabling connection of a power supply charge cable to the external adjustment device 400. In some embodiments, the recharging circuit may enable wireless charging of the internal power storage device 420, using induction to wirelessly transfer power. In some embodiments, the recharging circuit may be part of and connected to one or more of the power distribution board 421 and the power storage device 400.

In the illustrated embodiment, the power storage device 420 is a battery. The battery 420 may be mounted to a chassis of the external adjustment device 400, adjacent to a surface of the external adjustment device 400 enabling connection of a power supply to the external adjustment device 400 at a power supply input 422. The battery 420 includes a power interface board 421, configured to interface with and communicate power to the actuator 430. The power interface board 421 may be operably coupled to one or more of the actuator 430 and the control interface board 411. The power interface board 421 may also communicate electrical energy from one or more of a power supply input 422 and the power storage device 420, to the controller 410.

In certain embodiments, the actuator 430 of the external adjustment device 400 may include an electronic motor. The driver of the external adjustment device 400 may include a magnet 440 rotatably coupled to the actuator 430. The actuator 430 may be operably connected to one or more of the controller 410, the control interface board 411, the power interface board 421 and the internal power storage device 420. In the illustrated embodiment, the actuator 430, e.g., the electronic motor, is operably connected to the internal power storage device 420 by the power interface board 421. The power interface board 421 may include power distribution circuits to communicate electrical energy to the actuator 430 from one or more of the power supply input 422 and the internal power storage device 420. The power interface board 421 may also be operably connected to the control interface board 411, to relay control information from the controller 410 to the actuator 430. In some embodiments, the controller 410 may be in direct communication with the actuator 430, and in some embodiments the controller 410 may be connected to the electronic motor via a wireless connection, for example a Bluetooth® connection.

The actuator 430 may include any type of motor capable of rotating the magnet 440. The actuator 430 may be an electric motor and may include a rotational speed sensor 432. The rotational speed sensor 432 may be connected to and in communication with one or more of the control interface board 411 and the controller 410. In some embodiments, the internal speed sensor 432 may include for example one or more of an encoder and a digital output of an electronic motor. In some embodiments, the actuator 430 is configured to communicate rotational speed data to the controller 410 wirelessly.

Figure 8:
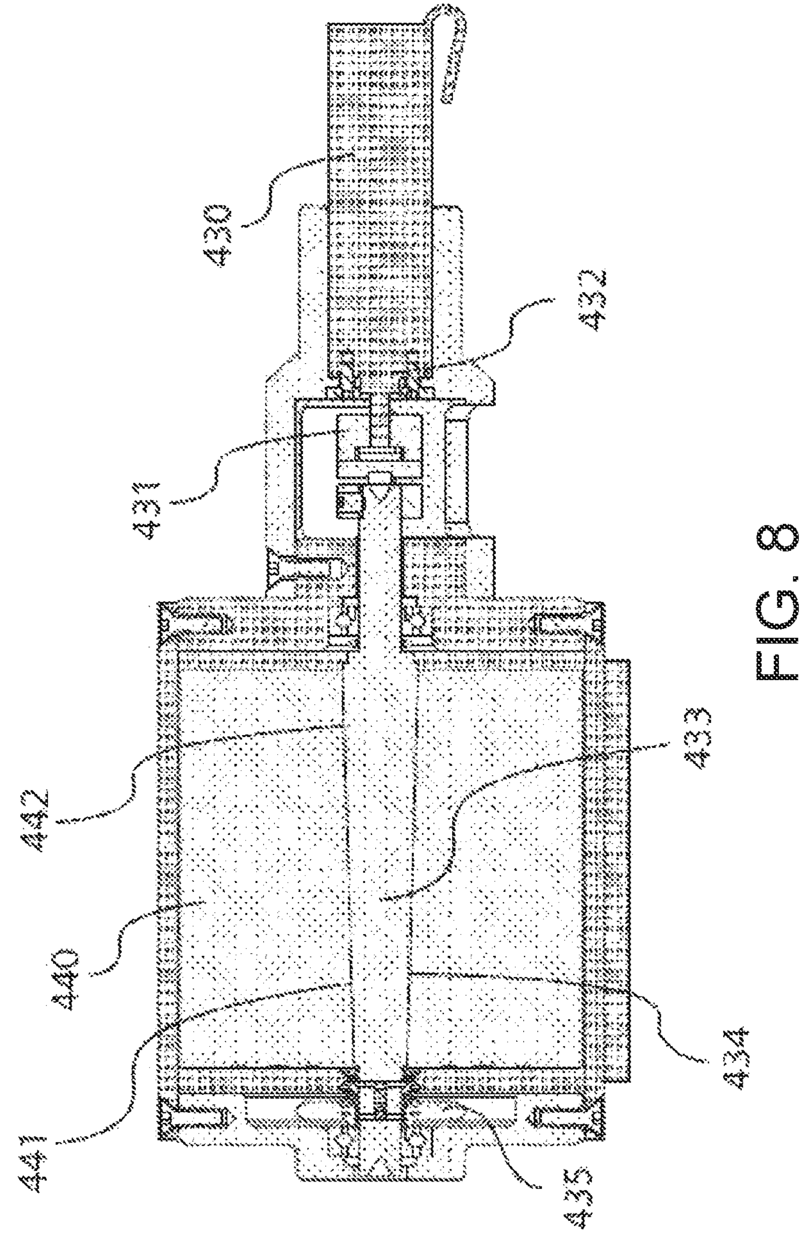
FIG. 8 shows a cross-sectional view of a magnet drive system including a motor having an internal motor speed sensor.

FIG. 8 shows an enhanced cross-sectional view of the actuator 430 and the magnet 440 of the external adjustment device 400 in accordance with a first embodiment. The magnet 440 is shown rotatably coupled to the actuator 430 by one or more couplings 431. In the illustrated embodiment, the magnet 440 includes an internal cavity 441 having an internal surface 442 and having a tapered profile. A magnet drive shaft 433 is shown including a magnet contact surface 434 having a tapered profile. The tapered profile of the magnet drive shaft 433 is configured to communicate with the tapered profile of the internal surface 442 of the magnet 440. This enables the magnet 440 to be secured to the magnet drive shaft 433 by a friction fit, the magnet 440 configured to be held onto the magnet drive shaft 433 by a cap 435 and the communicating tapered profiles. In some embodiments, the magnet 440 may be attached to the magnet drive shaft 433 using an adhesive material.

The magnet 440 may comprise any magnetic element including a radially polarized cylindrical magnet, a permanent magnet, an electromagnet, and any other magnetic element known and used in the art. The magnet 440 is configured to magnetically couple with a permanent magnet 118 of an adjustable implant 100 and to rotate the permanent magnet 118 and adjust the adjustable implant 100. Upon a rotation of the magnet 440, a rotating magnetic field will be generated, placing a force on the magnetically coupled permanent magnet 118 of the adjustable implant 100, thereby inducing a rotation of the permanent magnet 118 and subsequent adjustment of the adjustable implant 100.

In some embodiments, the external adjustment device 400 includes one or more sensors configured to monitor a rotational speed of the magnet 440. In some embodiments, the sensors include magnetic sensors, for example Hall-Effect sensors disposed on one or more of the housing 401, a plate, and a chassis, and may be placed adjacent to the magnet 440. In some embodiments, the sensors include photo-sensors. The magnet may include one or more circular optical encoder strips to work in conjunction with the photo-sensors. U.S. patent application Ser. No. 14/932,904, filed Nov. 4, 2015, describes various systems and methods for non-invasively detecting the force generated by a non-invasively adjustable implant, the entire contents of which are hereby incorporated by reference.

In the illustrated embodiment the external adjustment device 400 includes an actuator 430 having one or more rotational speed sensor 432 configured to detect a change in a motor angular velocity (V), and thereby non-invasively detect a rotation of the permanent magnet 118 of the adjustable implant 100. The actuator 430 has torque characteristics that allows for little variation in motor angular velocity (V) during a motor rotation and corresponding magnet 440 rotation, when there is no implant or ferrous material located near the ERC magnet or magnetically coupled to the magnet 440.

When an adjustable implant 100 having a magnet 202 (FIG. 2) is in close proximity to the rotating magnet 440, and for example magnet 202 is magnetically coupled to rotating magnet 440, the magnetic poles of both magnets cause a changing load on the actuator 430 twice per revolution. This causes the magnet 440 to increase or decrease in angular velocity, with the variations detectable by the rotational speed sensor 432.

Figures 9, 10, 11:
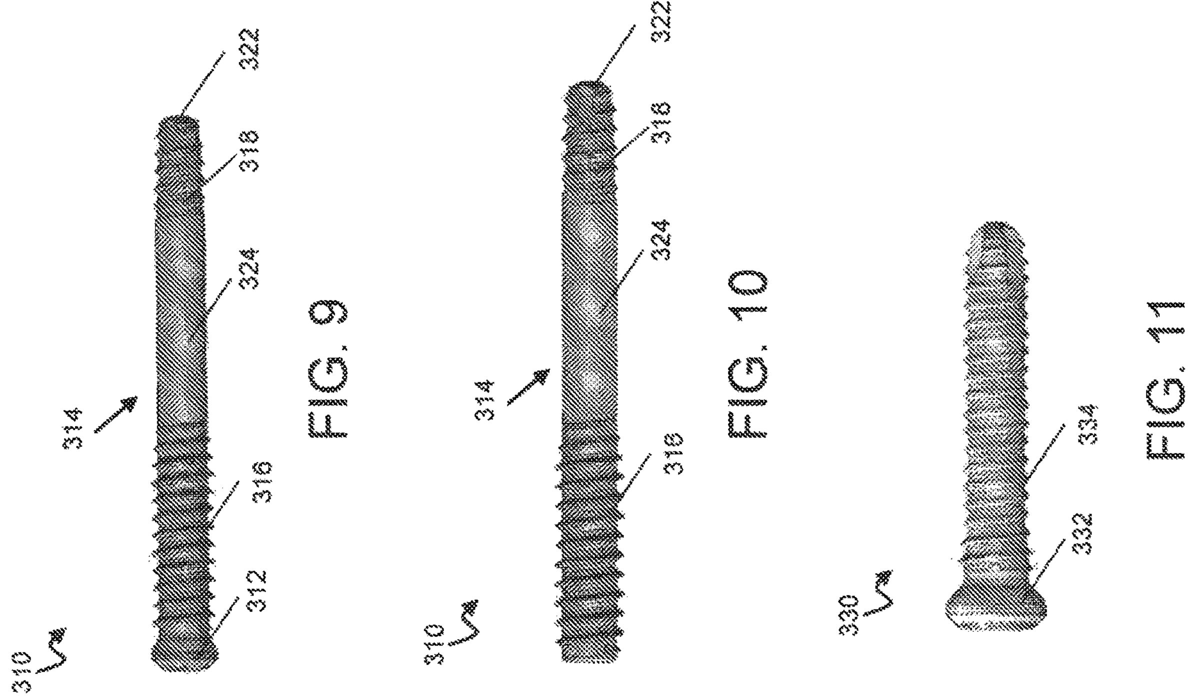
FIGS. 9-11 show embodiments of fixation screws according to the disclosure.

Turning now to FIG. 9, a fixation screw 310 used to couple the housing 102 to the calcaneus is shown. The fixation screw 310 includes a head 312 and a shank 314. The shank 314 includes a first threaded portion 316 adjacent the head 312, a second threaded portion 318 adjacent a distal tip 322 of the shank 314 and a non-threaded portion 324 extending therebetween. In another embodiment (FIG. 10), the fixation screw 310 is headless. FIG. 11 shows a fixation screw 330 used to couple the rod 106 to the tibia. Fixation screw 330 includes a head 332 and a fully threaded shank 334. It is to be understood that the fixation screws 310, 330 are merely exemplary and any other now known or later developed fixation screws can be used without departing from aspects of the disclosure. It is also to be understood that the fixation screws 310, 330 can have a variety of lengths and diameters to accommodate size of the bones and/or the device 100.

Turning now to FIGS. 1 and 12-25, aspects of the disclosure also include a method. The method includes providing an intramedullary device 100 including a housing 102 and a rod 106 configured to be moved relative to the housing 102. An incision is made on a plantar aspect of a calcaneus bone 120. As shown in FIG. 12, a guidewire 502 can be inserted into a retrograde fashion to indicate the intended path for the device 100. Specifically, the guidewire 502 is advanced through the calcaneus bone 120 and talus bone 124 into the intramedullary canal of the distal tibia bone 122. A soft tissue protector 504 is inserted over the guidewire 502. As shown in FIG. 13, the protector 504 includes a tubular portion 506 for accommodating instruments therein (e.g., guidewire 502 and reamer 510) and protecting the surrounding soft tissue. Additionally, the protector 504 includes a handle portion 508 for a medical professional to grasp and manipulate the protector 504. Returning to FIG. 12, a reamer 510 is positioned over the guidewire 502 and within the soft tissue protector 504 to create the pathway for the device 100 to be inserted. A second guidewire such as a ball-tipped guidewire (not shown) is exchanged with the guidewire 502 and the bone can be reamed at desired increments such as, for example, half millimeter increments, until the desired distance corresponding to the pre-distracted length of the device 100 is reached.

Figure 16:
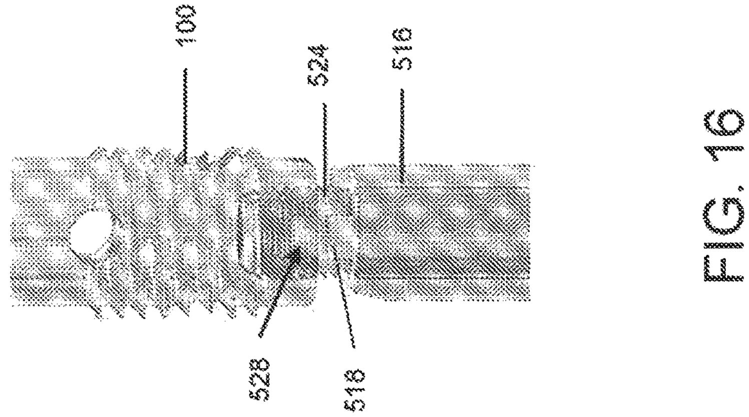
FIG. 16 shows an enlarged side view of the mating interface of the insertion handle, the intramedullary device, and the locking bolt according to embodiments of the disclosure.
Figure 15:
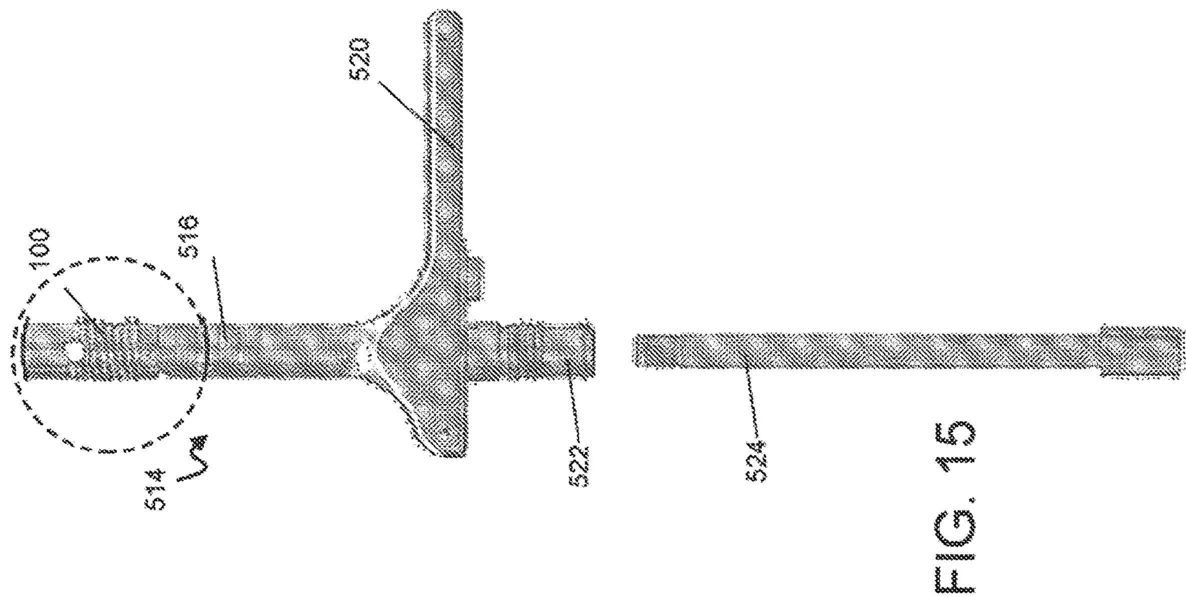
FIG. 15 shows the insertion handle, the intramedullary device, and the locking bolt according to embodiments of the disclosure.
Figure 17:
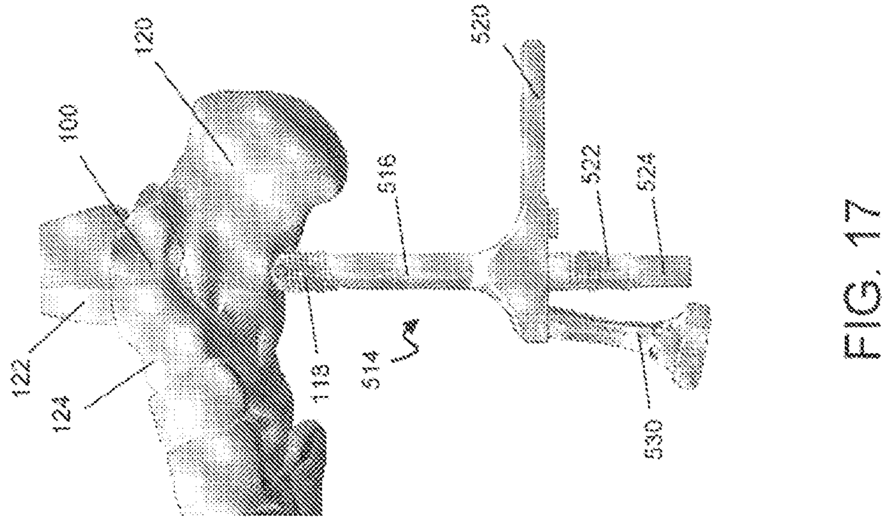
FIG. 17 shows insertion of the device into the calcaneus using the insertion handle and impactor according to embodiments of the disclosure.

Subsequently, the pre-distracted device 100 is inserted without the end cap 127. An insertion handle 514 can be used for insertion of the device. As shown in FIG. 14, the insertion handle 514 can be substantially T-shaped. The insertion handle 514 includes a tubular portion 516 having a device mating feature 518 at an end thereof for mating with the device 100. The insertion handle 514 also includes a handle portion 520 to be grasped by a medical professional during use. The handle portion 520 includes a grooved slot extending about a length thereof. As will be described herein, the grooved slot is configured to receive a fixation screw guide. The insertion handle 514 also includes a second tubular portion 522 that is communicatively coupled through the handle portion 520 to the first tubular portion 516 such that a channel extends between the tubular portions 514, 522 for passage of instruments therein. Turning now to FIG. 15, a locking bolt 524 having a threaded end is inserted into the tubular portion 516 through the tubular portion 522 to engage with an internal surface of the housing 102 of the device 100. More specifically, as shown in FIG. 16, the device mating feature 518 of the insertion handle 514 is aligned with and mated with cutouts 528 on the device 100 such that the device 100 is attached to the insertion handle 514. To maintain the position of the device 100 relative to the insertion handle, the locking bolt 524 extends into the housing 102 and the threads of the locking bolt 524 interact with the threads 129 (FIG. 2) of the internal surface of the housing 102 thereby locking the device 100, the insertion handle 514 and the locking bolt 524 together. As shown in FIG. 17, an impactor 530 can be attached to the insertion handle 514 and be used as a strike surface for mallet impaction.

Still referring to FIG. 17, the device 100 is inserted into the prepared calcaneus bone 120 after the guidewire 502 and soft tissue protector 504 have been removed. The impactor 530 can be struck with a mallet to aid in insertion. Once the threads 118 of the device 100 engage with the calcaneus bone 120, the impactor 530 can be removed and the insertion handle 514 can be rotated to advance the device 100 into the bone. The threads 118 of the device 100 aid in fixation stiffness to the calcaneus 120.

Figure 18:
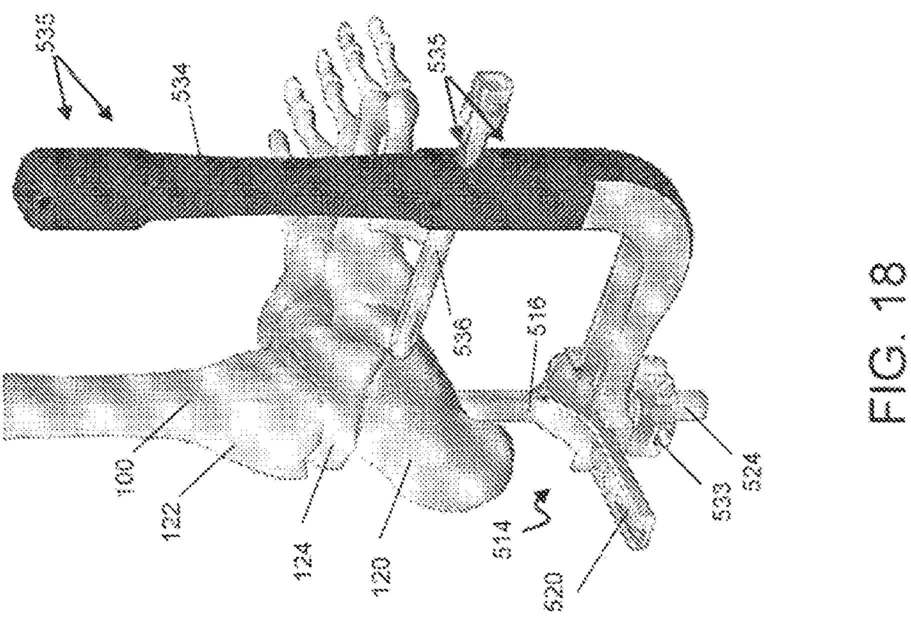

Once the device 100 is in the desired location relative to the bone(s), the fixation screws can be inserted to fix the device 100 to the bone(s). Specifically, the rod 106 is coupled to the tibia bone 122 of a patient and the housing 102 is coupled to the calcaneus bone 120 of a patient. As shown in FIG. 18, a guide 534 is attached to the insertion handle 514 in the medial-lateral orientation. More specifically, the tubular portion 522 of the locking handle 514 (having the locking bolt 524 positioned therein) is positioned within an aperture in the guide 534. The guide 534 can be locked relative to the insertion handle 514 via a locking nut 533 that threadingly engages an exterior of the tubular portion 522 (FIG. 18). The guide 534 includes fixation aperture guide holes 535 that are configured to be aligned with the fixation apertures 104, 105, 108 of the device 100. A guide tube 536 can be inserted into the guide hole 535 corresponding to the medial-lateral calcaneal fixation aperture 105 of the housing 102. A drill 538 (FIG. 19) is inserted into the guide tube 536 to prepare the pilot hole for the fixation screw 537 (FIG. 20). The fixation screw 537 can be inserted into the guide tube 536 and screwed into place such that the fixation screw 537 extends within the medial-lateral fixation aperture 105 of the housing 102 (FIGS. 1-2). Once the medial-lateral calcaneal fixation screw 537 is in place, the pre-loaded set screw 128 is tightened to lock the medial-lateral fixation screw 537. Specifically, a driver 539 is inserted into the cannulation of the locking bolt 516 to engage and screw the set screw 128 as shown in FIGS. 20-21.

Figures 22, 23:
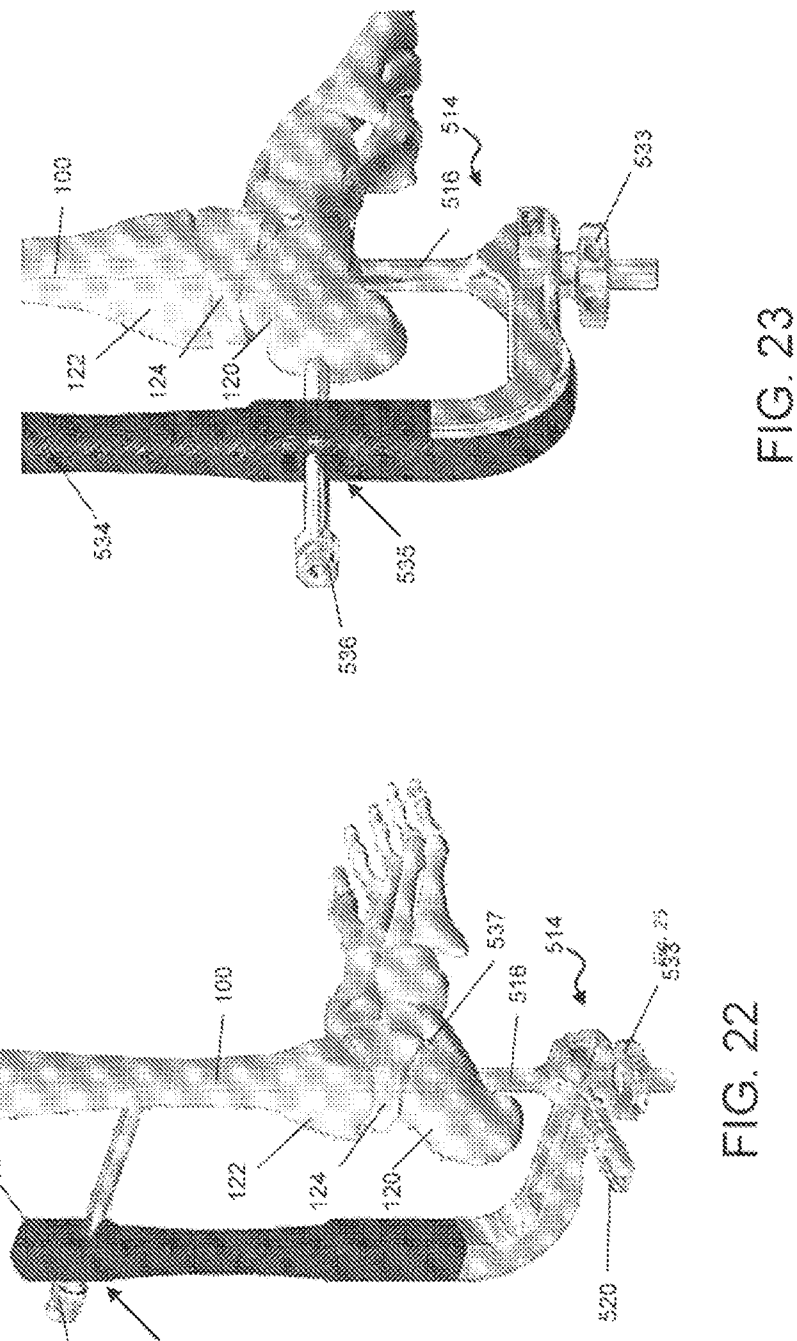
FIG. 22 shows using the guide for insertion of the medial-lateral tibia fixation screws according to embodiments of the disclosure.
FIG. 23 shows using the guide for insertion of the posterior-anterior calcaneus fixation screws according to embodiments of the disclosure.
Figure 25:
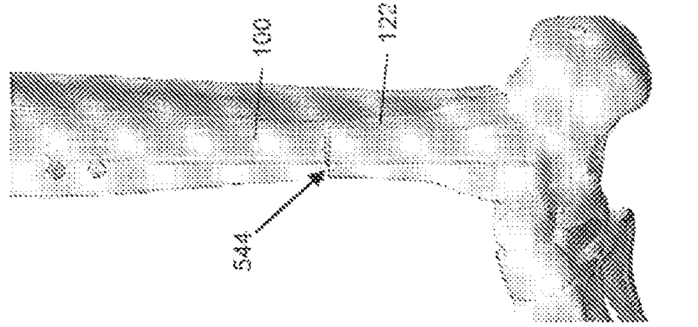
FIG. 25 shows creating an osteotomy to correct a limb length discrepancy via distraction osteogenesis according to embodiments of the disclosure.
Figure 24:
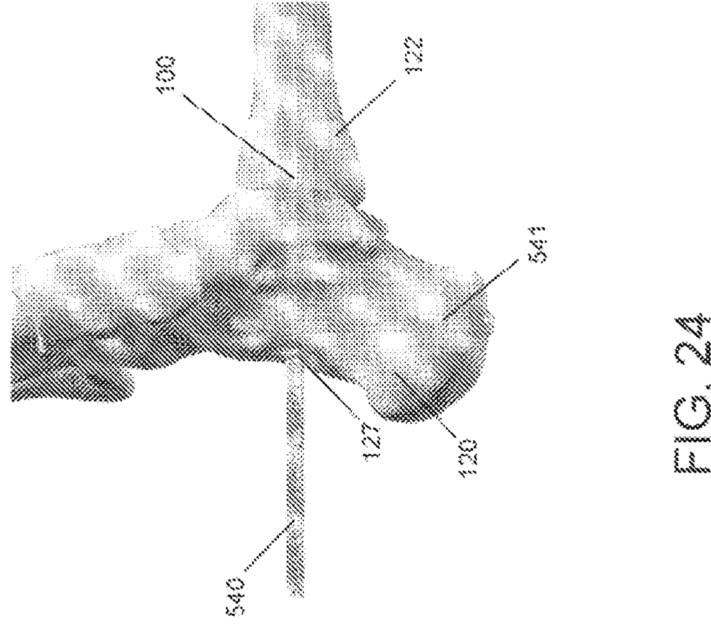
FIG. 24 shows insertion of the end cap into the device according to embodiments of the disclosure.

Next, the guide 534 is used to insert the medial-lateral tibial fixation screw(s) in much the same way. For example, as shown in FIG. 22, the locking bolt 533 can be loosened, thereby allowing about 180° of rotation of the guide 534, and then locking bolt 533 can be retightened to lock the guide 534 again relative to the locking handle 514. A guide tube 536 and drill (not shown) are used to insert the tibial fixation screws into the fixation aperture(s) 108 within the rod 106. Subsequently, as shown in FIG. 23, locking bolt 533 is loosened so that the guide 534 can be rotated 90° and retightened to lock the guide 534 again to the locking handle 514. A guide tube 536 is inserted into the guide hole 535 corresponding to the posterior-anterior calcaneal fixation aperture 104 of the housing 102. The process is repeated to prepare the pilot hole and insert a fixation screw 541 (FIG. 24) into the posterior-anterior fixation aperture 104, i.e., using the guide tube 536 and drill (not shown). Once all of the fixation screws have been inserted, the insertion handle 514 and guide 536 are removed and the end cap 127 can be screwed into the device 100 via a driver 540 as shown in FIG. 24. Specifically, the driver 540 is used to cause threaded engagement between the end cap 127 and the housing 102 of device 100.

With the device 100 implanted, the rod 106 is caused to retract relative to the housing 102 to cause compression about an ankle of the patient to cause ankle fusion. The retraction of the device 100 is controlled by an external adjustment device (e.g., external adjustment device 400) that is positioned external to the patient and configured to non-invasively retract the device 100 to cause compression about the ankle, across the tibio-talo-calcaneal (TTC) joint. The rate and frequency at which the retraction takes place can be determined by a medical professional.

After ankle fusion is achieved, it is possible that a limb length discrepancy may exist. More specifically, the limb on which ankle fusion was performed may be slightly shorter than the opposing limb. Thus, it may be desirable to correct the limb length discrepancy. To correct the limb length discrepancy, the device 100 is used without the need to implant an additional or supplemental device. More specifically, an osteotomy 544 (FIG. 25) is created within the tibia 122. The rod 106 is then distracted relative to the housing 102 to correct a limb length discrepancy of the patient by distraction osteogenesis. The distraction of the device 100 is controlled by an external adjustment device (e.g., external adjustment device 400) that is positioned external to the patient and configured to non-invasively distract the device 100.

Over the treatment period, the bone is regularly distracted. Regularly distracted is meant to indicate that distraction occurs on a regular or periodic basis which may be on the order of every day or every few days. An exemplary distraction rate is one millimeter per day, although, other distraction rates may be employed. That is to say, a typical distraction regimen may include a daily increase in the length of the device 100 by about one millimeter. This may be done, for example, by four distraction periods per day, each having 0.25 mm of distraction. The device 100, as disclosed in more detail below, has a magnetic drive system, which allows the rod 106 to be telescopically distracted relative to the housing 102, thus forcing the first section and the second section of the bone further apart to encourage osteogenesis.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B"; "one or more of A and B"; and "A and/or B" are each intended to mean "A alone, B alone, or A and B together." A similar interpretation is also intended for lists including three or more items. For example, the phrases "at least one of A, B, and C"; "one or more of A, B, and C"; and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups. As used herein, "substantially" refers to largely, for the most part, entirely specified or any slight deviation which provides the same technical benefits of the disclosure. As used herein, "approximately" is intended to include values, for example, within 10% of the stated values.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A method comprising:

providing an intramedullary device including:

a housing and a rod configured to be moved relative to the housing, wherein the housing defines a longitudinal axis and includes:

a first portion having a first diameter and a second portion, wherein the second portion comprises a smooth portion and a second diameter larger than the first diameter, and an external thread positioned distally from the second portion at a distal end of the housing, wherein a length of the smooth portion is greater than a length of the external thread;

a first fixation aperture positioned at least partially on the external thread and being perpendicular to the longitudinal axis;

a second fixation aperture positioned at least partially on the external thread and being perpendicular to both the longitudinal axis and the first fixation aperture;

coupling the rod to a tibia bone of a patient;

coupling the housing to a calcaneus bone of the patient; and non-invasively retracting the rod relative to the housing, thereby causing compression about an ankle of the patient to cause ankle fusion once the housing is coupled to the calcaneus bone, wherein the intramedullary device includes a magnetic drive system which allows the rod to be telescopically retracted relative to the housing, wherein the intramedullary device includes an end cap, the end cap being threadingly engageable with threads positioned about an inner surface of the housing, wherein the intramedullary device further includes a magnetic maintenance member having two spaced apart tabs and positioned in proximity to the magnetic drive system and configured to eliminate accidental actuation of the intramedullary device, and wherein the housing includes a lead screw which turns a nut secured to an inner surface adjacent to a cavity of the rod, the lead screw is mechanically coupled to a cylindrical permanent magnet of the magnetic drive system, wherein the rotation of the cylindrical magnet is driven by an external adjustment device, thereby causing rotation of the lead screw, wherein the cylindrical permanent magnet is positioned within a magnet housing which includes an axle which couples the magnet housing to a gear assembly, wherein the lead screw is configured to freely rotate within the cavity of the rod;

inserting the first fixation screw through the first fixation aperture and into the calcaneus bone;

inserting a second fixation screw through the second fixation aperture and into the calcaneus bone such that the inserted first and second fixation screws are perpendicular to each other and to the longitudinal axis.

2. The method of claim 1, further comprising:

after ankle fusion is achieved, non-invasively distracting the rod relative to the housing to correct a limb length discrepancy of the patient using an external adjustment device, and creating an osteotomy within the tibia after ankle fusion is achieved and prior to distracting the rod.

3. The method of claim 1, wherein non-invasively retracting the rod relative to the housing includes using an external adjustment device.

4. The method of claim 1, wherein the rod is configured to noninvasively distract and non-invasively retract relative to the housing.

5. The method of claim 1, wherein coupling the housing to the calcaneus bone of the patient further comprises:

tightening a set screw against the first fixation screw to lock the first fixation screw in place within the first fixation aperture affixing the end cap to the distal end of the housing.

6. The method of claim 5, wherein the first fixation aperture is oriented in a medial-lateral direction, and the second fixation aperture is oriented in a posterior-anterior direction.

7. The method of claim 5, wherein the set screw is disposed within the housing, and on an opposing side of the second fixation aperture relative to the end cap.

8. The method of claim 5, wherein the end cap is configured to act as a second set screw for the second fixation screw when affixed, thereby locking the second fixation screw in place within the second fixation aperture.

9. The method of claim 5, further comprising affixing the end cap to the distal end of the housing after inserting the first fixation screw, tightening the set screw, and inserting the second fixation screw, wherein affixing the end cap to the distal end of the housing comprises threadably engaging an internally threaded portion of the housing at the distal end thereof with an externally threaded portion of the end cap.

10. The method of claim 5, wherein the end cap is configured to sealably close the housing at the distal end thereof, and to provide a flush end to the intramedullary device to interface with the patient.

11. The method of claim 1, further comprising: wherein the intramedullary device further comprises a ramp configured to interface between the first portion and the second portion of the housing.

12. The method of claim 1, wherein the first diameter is between approximately 10 mm and approximately 13 mm, and the second diameter is between approximately 12 mm and approximately 15 mm.

13. The method of claim 1, wherein the external thread comprises a double lead thread, and wherein the external thread further comprises a thread pitch of approximately 2 mm.

14. The method of claim 1, further comprising, prior to coupling the housing to the calcaneus bone of the patient, inserting the intramedullary device into a plantar aspect of the calcaneus bone and toward the tibia bone;

malleting the intramedullary device until the external thread engages the calcaneus bone; and rotatably advancing the intramedullary device into the calcaneus bone, wherein the external thread is configured to provide fixation stiffness to the calcaneus bone.

15. The method of claim 1, wherein the external thread is a double lead thread.

* * * * *